(12) United States Patent
Masatoshi et al.

(10) Patent No.: US 8,198,491 B2
(45) Date of Patent: Jun. 12, 2012

(54) PROCESS FOR PREPARING 2,3,3,3-TETRAFLUOROPROPENE AND 1,3,3,3-TETRAFLUOROPROPENE

(75) Inventors: Nose Masatoshi, Settsu (JP); Komatsu Yuzo, Settsu (JP); Sugiyama Akinari, Settsu (JP); Shibanuma Takashi, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 13/057,525

(22) PCT Filed: Jul. 21, 2009

(86) PCT No.: PCT/JP2009/063314
§ 371 (c)(1),
(2), (4) Date: Feb. 4, 2011

(87) PCT Pub. No.: WO2010/016401
PCT Pub. Date: Feb. 11, 2010

(65) Prior Publication Data
US 2011/0137090 A1     Jun. 9, 2011

Related U.S. Application Data

(60) Provisional application No. 61/086,540, filed on Aug. 6, 2008.

(51) Int. Cl.
C07C 17/00 (2006.01)
C07C 17/02 (2006.01)
(52) U.S. Cl. .................... 570/156; 570/154
(58) Field of Classification Search ............... 570/154, 570/156
See application file for complete search history.

(56) References Cited

U.S. PATENT DOCUMENTS

| | | | |
|---|---|---|---|
| 2,931,840 A | 4/1960 | Marquis | |
| 3,996,299 A | 12/1976 | Fozzard | |
| 5,986,151 A | 11/1999 | Van Der Puy | |
| 6,124,510 A | 9/2000 | Elsheikh et al. | |
| 7,722,781 B2 | 5/2010 | Rao et al. | |
| 7,833,434 B2 | 11/2010 | Rao et al. | |
| 2005/0245773 A1 | 11/2005 | Mukhopadhyay et al. | |
| 2006/0258891 A1 | 11/2006 | Mukhopadhyay et al. | |
| 2008/0051611 A1 | 2/2008 | Wang et al. | |
| 2009/0127496 A1 | 5/2009 | Rao et al. | |
| 2009/0264689 A1 | 10/2009 | Rao et al. | |
| 2010/0200798 A1 | 8/2010 | Rao et al. | |

FOREIGN PATENT DOCUMENTS

| | | |
|---|---|---|
| EP | 0 974 571 | 1/2000 |
| JP | 63-211245 | 9/1988 |
| JP | 11-140002 | 5/1999 |
| JP | 2007-320896 | 12/2007 |
| WO | 2008/002499 | 1/2008 |
| WO | 2008/002500 | 1/2008 |
| WO | 2008/030440 | 3/2008 |

OTHER PUBLICATIONS

International Search Report issued Mar. 3, 2010 in International (PCT) Application No. PCT/JP2009/063314.
PCT Written Opinion of the International Searching Authority issued Mar. 3, 2010 in International (PCT) Application No. PCT/JP2009/063314.
Haszeldine et al., "Addition of Free Radicals to Unsaturated Systems. Part XIII. Direction of Radical Addition to Chloro-1:1-difluoroethylene" J. Chem. Soc., pp. 2193-2197 (1957).
Haszeldine et al., "Free-Radical Additions to Unsaturated Systems. Part XVII. Reaction of Trifluoroiodomethane with Mixtures of Ethylene and Vinyl Fluoride and of Ethylene and Propene", J. Chem. Soc., vol. 3, pp. 414-421 (1970).
Banks et al., "Preparation of 2,3,3,3-tetrafluoropropene from Trifluoroacetylacetone and Sulphur Tetrafluoride", J. Fluorine Chem., vol. 82, pp. 171-174 (1997).

*Primary Examiner* — Jafar Parsa
(74) *Attorney, Agent, or Firm* — Wenderoth, Lind & Ponack, L.L.P.

(57) ABSTRACT

The present invention provides a process for preparing 2,3,3,3-tetrafluoropropene represented by $CF_3CF=CH_2$ and 1,3,3,3-tetrafluoropropene represented by $CF_3CH=CHF$, in which 3,3,3-trifluoropropyne represented by the chemical formula $CF_3C\equiv CH$ is reacted with hydrogen fluoride under heating. The process of the present invention is a simple, effective and industrially applicable process for preparing 2,3,3,3-tetrafluoropropene and 1,3,3,3-tetrafluoropropene.

8 Claims, No Drawings

PROCESS FOR PREPARING 2,3,3,3-TETRAFLUOROPROPENE AND 1,3,3,3-TETRAFLUOROPROPENE

This application claims priority based on U.S. Provisional Application No. 61/086,540 filed Aug. 6, 2008.

TECHNICAL FIELD

The present invention relates to a process for preparing 2,3,3,3-tetrafluoropropene and 1,3,3,3-tetrafluoropropene.

BACKGROUND ART 2,3,3,3-Tetrafluoropropene represented by the chemical formula $CF_3CF\!=\!CH_2$ (HFC-1234yf) and 1,3,3,3-tetrafluoropropene represented by the chemical formula $CF_3CH\!=\!CHF$ (HFC-1234ze) are both compounds that are useful as refrigerants, and have been receiving attention for use as constituents of refrigerants or mixed refrigerants that can be used as alternatives for chlorofluorocarbon.

In connection with these compounds, Non-Patent Literature (NPL) 1 listed below, for example, discloses an HFC-1234yf preparation method comprising a single step of subjecting a compound represented by $CF_3CF_2CH_2X$ (X is Cl or I) to a reaction with zinc in ethanol. However, this method is not preferable as an industrial-scale production method, since zinc is expensive and a large amount of waste is generated.

In addition to the above, the following patent literature, etc., discloses methods for producing HFC-1234yf. Patent Literature (PTL) 1 discloses a method comprising reacting chloromethyl tetrafluoropropanate with amine; Patent Literature 2 discloses a method comprising the thermal decomposition of 1-trifluoromethyl-1,2,2-trifluorocyclobutane; Patent Literature 3 discloses a method comprising reacting chlorotrifluoroethylene ($CClF\!=\!CF_2$) and methyl fluoride ($CH_3F$) in the presence of a Lewis acid such as $SbF_5$; and Patent Literature 4 discloses a method comprising the thermal decomposition of tetrafluoroethylene ($CF_2\!=\!CF_2$) and chloromethane ($CH_3Cl$). Non-Patent Literatures 2 and 3 listed below also disclose HFC-1234yf production methods.

These processes, however, are not considered to be effective for industrial purposes since the starting materials are difficult to produce and are not easily obtained, the reaction conditions are severe, the reaction reagents are expensive, the yield is low, etc.

As a method for producing HFC-1234ze, known methods include a method comprising dehydrofluorination of $CF_3CH_2CHF_2$ (HFC-245fa) (see Patent Literatures 5 to 8); a method comprising dehydrofluorination of $CF_3CHFCH_2F$ (HFC-245eb) (see Patent Literatures 9 to 10); a method comprising fluorination of $CF_3CH\!=\!CHCl$ (HCFC-1233zd) (Patent Literature 11); and the like. However, these processes need to be improved for industrial usage since the starting materials are difficult to produce and are not easily obtained, the yield is low, multi-stage steps are required, etc.

CITATION LIST

Patent Literature

PTL 1: Japanese Unexamined Patent Application No. 63-211245
PTL 2: U.S. Pat. No. 3,996,299
PTL 3: U.S. Patent Application Publication No. 2006/258891
PTL 4: U.S. Pat. No. 2,931,840
PTL 5: U.S. Patent Application Publication No. 2005/0245773
PTL 6: U.S. Patent Application Publication No. 2008/051611
PTL 7: EP 2000/974571 A2
PTL 8: Japanese Unexamined Patent Application No. 11-140002
PTL 9: WO 2008/002499 A2
PTL 10: WO 2008/002500 A1
PTL 11: Japanese Unexamined Patent Application No. 2007-320896

Non Patent Literature

NPL 1: J. Chem. Soc., 1957, 2193-2197
NPL 2: J. Chem. Soc., 1970, 3, 414-421
NPL 3: J. Fluorine Chem., 1997, 82, 171-174

SUMMARY OF INVENTION

Technical Problem

The present invention has been accomplished in view of the foregoing problems found in the prior art. A main object of the present invention is to provide a simple, effective and industrially applicable process for preparing 2,3,3,3-tetrafluoropropene and 1,3,3,3-tetrafluoropropene.

Solution to Problem

The present inventors conducted extensive research to achieve the above object, and found the following. That is, 2,3,3,3-tetrafluoropropene and 1,3,3,3-tetrafluoropropene can be prepared in a single-step reaction by using, as starting materials, 3,3,3-trifluoropropyne represented by the chemical formula $CF_3C\!\equiv\!CH$ and hydrogen fluoride, and allowing the starting materials to react with each other under heating. Such a process can be an industrially advantageous preparation process of the compounds. The present invention was thereby completed.

Specifically, the present invention provides the following processes for preparing 2,3,3,3-tetrafluoropropene and 1,3,3,3-tetrafluoropropene.

1. A process for preparing 2,3,3,3-tetrafluoropropene represented by $CF_3CF\!=\!CH_2$ and 1,3,3,3-tetrafluoropropene represented by $CF_3CH\!=\!CHF$, the process comprising reacting 3,3,3-trifluoropropyne represented by the chemical formula $CF_3C\!\equiv\!CH$ with hydrogen fluoride under heating.
2. The process according to Item 1, wherein the reaction is carried out in a gas phase.
3. The process according to Item 1 or 2, wherein the reaction is carried out in the presence of a catalyst.
4. The process according to any of Items 1 to 3, wherein the reaction is carried out in the presence of chromium oxide or fluorinated chromium oxide as a catalyst.

In the present invention, 3,3,3-trifluoropropyne represented by the chemical formula $CF_3C\!\equiv\!CH$ and hydrogen fluoride (HF) are used as starting materials. 3,3,3-Trifluoropropyne is a readily available known substance, which can be easily prepared by a method disclosed in, for example, J. Chem. Soc. 1951, pp 2495-2504; J. American Chem. Soc. 1951, 73, pp 1042-1043; J. Chem. Soc. 1952, pp 3483-3490; U.S. Pat. No. 106,318; or the like.

In the process of the present invention, 3,3,3-trifluoropropyne represented by the chemical formula $CF_3C\!\equiv\!CH$ is reacted with hydrogen fluoride in the presence or absence of a catalyst under heating. Thereby, 2,3,3,3-tetrafluoropropene represented by chemical formula $CF_3CF=CH_2$ and 1,3,3,3-tetrafluoropropene represented by chemical formula $CF_3CH=CHF$ are prepared.

A specific embodiment of the preparation process according to the present invention is not particularly limited. For example, a catalyst, when utilized, is placed into a tubular flow reactor, into which starting materials of 3,3,3-trifluoropropyne and hydrogen fluoride are introduced. Examples of the usable flow reactors include adiabatic reactors, multitubular reactors cooled using a heat transmitting medium, and the like. The reactors usable herein are preferably made of a material that has resistance to corrosion, such as Hastelloy, Inconel, Monel, or the like.

Examples of the usable catalysts include, but are not limited to, metal oxides, fluorinated metal oxides, metal fluorides, and the like. Preferred among these are chromium oxide catalysts, fluorinated chromium oxide catalysts, aluminium oxide catalysts, fluorinated aluminium oxide catalysts, and the like. The above fluorination catalysts may be supported on a carrier such as alumina, activated carbon, and the like.

Of these catalysts, with respect to chromium oxides, there is no limitation on their composition; however, those having a composition formula $CrO_m$, wherein m is preferably in the range of $1.5<m<3$, more preferably $2<m<2.75$, and particularly preferably $2<m<2.3$, can be utilized. The following is an example of a preparation method of such chromium oxides.

First, an aqueous chromium salt solution (chromium nitrate, chromium chloride, chromium alum, chromium sulfate, or the like) and aqueous ammonia are mixed to obtain a precipitate of chromium hydroxide. For example, a precipitate of chromium hydroxide may be obtained by adding, to a 5.7% aqueous chromium nitrate solution, 10% aqueous ammonia dropwise in an amount from 1 to about 1.2 equivalent weight of ammonia per equivalent weight of chromium nitrate. The properties of chromium hydroxide may be controlled by the reaction rate during the precipitation. The reaction rate is preferably fast. Better catalytic activity is achieved as the reaction rate increases. The reaction rate varies depending upon the temperature of the reaction solution, mixing procedure (mixing speed) of the aqueous ammonia, stirring conditions, etc. Accordingly, the adjustment of these conditions enables control of the reaction rate.

The obtained precipitate is filtrated, washed, and then dried. The drying may be carried out, for example, in air, at about 70 to about 200° C., preferably at about 120° C., for about 1 to about 100 hours, preferably about 12 hours. The product at this stage is referred to as a chromium hydroxide state. Subsequently, the dried product is disintegrated into a powder. The rate of the precipitation is adjusted prior to disintegration so that the disintegrated powder (for example, having a particle diameter of 1,000 μm or less, and 95% of the disintegrated powder have a particle diameter from 46 to 1,000 μm) has a density of about 0.6 to about 1.1 g/ml, preferably about 0.6 to about 1.0 g/ml. A powder density less than 0.6 g/ml is not preferable, since the pellet strength will be insufficient. Conversely, a powder density more than 1.1 g/ml is not preferable, since the catalyst activity will be degraded, and the pellets will break easily. The specific surface area of the powder is preferably about 100 $m^2$/g or more, and more preferably about 120 $m^2$/g or more, under degassing conditions at 200° C. for 80 minutes. The specific surface area used herein is referred to as a value measured by the BET method.

The obtained chromium hydroxide powder is formed into pellets by means of a tableting machine. If necessary, the chromium hydroxide powder may be mixed with graphite in an amount of about 3 wt % or less. The pellets may have a diameter of, for example, about 3.0 mm, and a height of about 3.0 mm. The pellets preferably have a compressing strength (pellet strength) of about 210±40 kg/$cm^2$. A compressing strength that is too high lowers the contact efficiency of gas. This causes the deterioration of catalytic activity, as well as the formation of pellets that can be easily broken. Conversely, a compressing strength that is too low causes the pellets to be easily pulverized, making the handling thereof difficult.

The formed pellets are fired in an inert atmosphere, e.g., in a nitrogen stream, to yield an amorphous chromium oxide. The firing temperature is preferably 360° C. or more. However, when the temperature is too high, the pellets will be crystallized. For this reason, the temperature is preferably as high as possible, but within a range that can prevent the crystallization. For example, the firing may be performed, at about 380 to about 460° C., preferably at about 400° C. for about 1 to 5 hours, preferably for about 2 hours.

The specific surface area of the fired chromium oxide may be about 170 $m^2$/g or more, preferably about 180 $m^2$/g or more, and more preferably about 200 $m^2$/g or more. The upper limit of the specific surface area may be about 240 $m^2$/g, and more preferably about 220 $m^2$/g. A specific surface area of the fired chromium oxide that is more than 240 $m^2$/g results in, although the catalytic activity will be enhanced, an increased deterioration rate. Conversely, a specific surface area less than 170 $m^2$/g results in the decreased catalytic activity, and is thus not preferable.

A fluorinated chromium oxide may be prepared according to the method disclosed in the Japanese Unexamined Patent Publication No. 5-146680. For example, the chromium oxide obtained in the above method is fluorinated with hydrogen fluoride (HF treatment) to thereby obtain a fluorinated chromium oxide. The fluorination temperature may be adjusted so that the water to be generated is not condensed (for example, about 150° C. at 1 atmospheric pressure). The upper limit of the temperature may be adjusted to a value where the catalyst does not undergo crystallization due to the heat of reaction. The pressure during the fluorination is not limited, but is preferably the same pressure as the pressure at which the catalyst will be used for the catalytic reaction. The fluorination temperature may be, for example, about 100 to about 460° C.

The catalytic surface area is reduced by fluorination treatment. Generally, a greater specific surface area leads to a higher catalytic activity. The specific surface area after the fluorination may preferably be about 25 to about 130 $m^2$/g, and more preferably about 40 to about 100 $m^2$/g, but is not limited to this range.

The fluorination reaction of the chromium oxide may be carried out by supplying hydrogen fluoride to a reactor containing chromium oxide, prior to carrying out the process of the present invention described hereinafter. After chromium oxide is fluorinated as above, the reaction for producing 2,3,3,3-tetrafluoropropene and 1,3,3,3-tetrafluoropropene can be proceeded by supplying the starting materials to the reactor. The extent of fluorination is not limited, but the fluorine content is preferably about 10 to about 30 wt. %.

The chromium catalysts disclosed in Japanese Unexamined Patent Publication No. 11-171806 may also be used as a chromium oxide catalyst or fluorinated chromium oxide catalyst. Specifically, the chromium catalysts, which are in an amorphous state, comprise a chromium compound as a main component, to which at least one metal element selected from the group consisting of indium, gallium, cobalt, nickel, zinc and aluminum is added, wherein the average valence of the chromium in said chromium compound being +3.5 or more and +5.0 or less.

The catalyst comprising the chromium oxide or fluorinated chromium oxide mentioned above may be supported on a carrier such as alumina, activated carbon, and the like.

In the present invention, the proportion of 3,3,3-trifluoropropyne to hydrogen fluoride, which are used as starting materials, is not limited. For example, hydrogen fluoride may be used in an amount of 1 mole or more per 1 mole of 3,3,3-trifluoropropyne. Preferably, hydrogen fluoride is used in an amount of about 1 to about 3 moles per mole of 3,3,3-trifluoropropyne.

The starting materials mentioned above may be directly supplied to a reactor, or may be diluted with an inert gas such as nitrogen, helium, argon, or the like, to be supplied to a reactor.

Further, the above starting materials may be supplied together with oxygen in order to maintain long-term catalytic activity. When oxygen is supplied, the amount thereof may be about 0.1 to about 5 mol %, based on the total moles of the starting materials, 3,3,3-trifluoropropyne and hydrogen fluoride, to be supplied.

The inside of the reactor may be heated to a temperature that is high enough to generate a reaction of 3,3,3-trifluoropropyne and hydrogen fluoride. The reaction temperature may be lowered with the use of a catalyst. The temperature inside the reactor may be, for example, about 50 to 500° C. with the use of a catalyst. When the reaction is carried out in a gas phase, the temperature is more preferably about 200 to about 400° C. When the temperature is higher than this range, the catalytic activity will be degraded. Conversely, when the temperature is lower than this range, the conversion rate of the starting materials will decrease, and thus is not preferable.

The pressure during the reaction is not limited and the reaction may be carried out under normal pressure or increased pressure. Specifically, the fluorination reaction of the present invention may be carried out under atmospheric pressure (0.1 MPa). The reaction may also be carried out under increased pressure of about 2.0 MPa or less.

The reaction time is not particularly limited. However, when the reaction is carried out in a gas phase in the presence of a catalyst, the contact time, which is usually determined by $W/F_o$, may be adjusted to a range of 0.1 to 30 g·sec/cc, preferably about 1.0 to about 10 g·sec/cc. $W/F_o$ is a ratio of a catalyst weight W (g) to a total flow rate $F_o$ (flow rate at 0° C., 1 atm: cc/sec) of starting material gas (i.e., 3,3,3-trifluoropropyne and hydrogen fluoride), an inert gas and oxygen that are introduced to a reaction system.

In the process of the present invention, when the reaction temperature is as high as about 300° C. or more, the selectivity of 2,3,3,3-tetrafluoropropene (HFC-1234yf) can be improved by a longer contact time. For this reason, the adjustment of the reaction temperature and contact time enables the control of the target product production ratio of 2,3,3,3-tetrafluoropropene (HFC-1234yf) to 1,3,3,3-tetrafluoropropene (HFC-1234ze-E+Z).

At the reactor outlet, a reaction product comprising 2,3,3,3-tetrafluoropropene (HFC-1234yf) and 1,3,3,3-tetrafluoropropene (HFC-1234ze-E+Z) can be obtained. 1,3,3,3-tetrafluoropropene is obtained as a mixture of E- and Z-forms.

The reaction product may be collected by isolation and purification. The unreacted 3,3,3-trifluoropropyne may be recycled after the isolation and purification process by returning it to the reactor. As explained above, since the unreacted product may be recycled, even when the conversion ratio of the starting material is low, a high productivity can be maintained.

2,3,3,3-Tetrafluoropropene (HFC-1234yf) and 1,3,3,3-tetrafluoropropene (HFC-1234ze-E+Z) may be used as a mixture as is, or may be separated to be used individually.

Advantageous Effects of Invention

According to the process of the present invention, the target products of 2,3,3,3-tetrafluoropropene (HFC-1234yf) and 1,3,3,3-tetrafluoropropene (HFC-1234 ze-E+Z) can be prepared in a single-step reaction at a high yield, using the readily obtainable starting materials of 3,3,3-trifluoropropyne and hydrogen fluoride.

DESCRIPTION OF EMBODIMENTS

The present invention will be described below in more detail with reference to the examples.

EXAMPLE 1

An amount of 6.0 g of catalyst (fluorine content: about 15.0 wt. %), which had been obtained by subjecting a chromium oxide represented by the composition formula $CrO_{2.0}$ to fluorination treatment, was placed into a tubular Hastelloy reactor having an inside diameter of 15 mm and a length of 1 m. While the reactor was maintained at atmospheric pressure (1 atm) at 250° C., 60 cc/min of anhydrous hydrogen fluoride (HF) (flow rate at 0° C., 1 atm) and 90 cc/min of nitrogen ($N_2$) (flow rate at 0° C., 1 atm) were supplied to the reactor for 1 hour. Thereafter, $CF_3C\equiv CH$ (3,3,3-trifluoropropyne; bp.: −48° C.; purity: 97.7%; purchased from Lancaster (Great Britain)) was supplied at a rate of 30 cc/min (flow rate at 0° C., 1 atm), and the reactor temperature was changed to 221° C. The molar ratio of HF to $CF_3C\equiv CH$ was 2, and the contact time ($W/F_0$) was 2.0 g·sec/cc. One hour after the reaction temperature became the target reaction temperature, the outlet gas from the reactor was analyzed using gas chromatography. Table 1 shows the result. The structures of the resulting products were as follows.

$CF_3CF\!=\!CH_2$ (HFC-1234yf)
$CF_3CH\!=\!CHF$ (HFC-1234ze-E)
$CF_3CH\!=\!CHF$ (HFC-1234ze-Z)
$CF_3CF_2CH_3$ (HFC-245cb)
$CF_3CH_2CHF_2$ (HFC-245fa)

EXAMPLE 2

The same process was carried out in the same manner as in Example 1 except that the amount of the catalyst used was changed to 18.0 g. The molar ratio of HF to $CF_3C\equiv CH$ was 2, and contact time ($W/F_0$) was 6.0 g·sec/cc. Table 1 shows the results of analysis.

EXAMPLE 3

The same process was carried out in the same manner as in Example 1 except that the temperature was changed to 269° C. The molar ratio of HF to $CF_3C\equiv CH$ was 2, and the contact time ($W/F_0$) was 2.0 g·sec/cc. Table 1 shows the result of analysis.

EXAMPLE 4

The same process was carried out in the same manner as in Example 1 except that the temperature was changed to 320°

C. The molar ratio of HF to $CF_3C\equiv CH$ was 2, and the contact time ($W/F_0$) was 2.0 g·sec/cc. Table 1 shows the result of analysis.

EXAMPLE 5

The same process was carried out in the same manner as in Example 1 except that the temperature was changed to 371° C. The molar ratio of HF to $CF_3C\equiv CH$ was 2, and the contact time ($W/F_0$) was 2.0 g·sec/cc. Table 1 shows the result of analysis.

EXAMPLE 6

The same process was carried out in the same manner as in Example 5 except that the amount of the catalyst used was changed to 30.0 g. The molar ratio of HF to $CF_3C\equiv CH$ was 2, and the contact time ($W/F_0$) was 10.0 g·sec/cc. Table 1 shows the result of analysis.

TABLE 1

|  | Ex. 1 | Ex. 2 | Ex. 3 | Ex. 4 | Ex. 5 | Ex. 6 |
| --- | --- | --- | --- | --- | --- | --- |
| Reaction Temperature (° C.) | 221 | 221 | 269 | 320 | 371 | 371 |
| $CF_3C\equiv CH$ Conversion (%) | 7.8 | 18.8 | 26.8 | 92.8 | 75.6 | 70.8 |
| Product Selectivity (%) | | | | | | |
| HFC-1234yf | 12.6 | 12.3 | 11.1 | 3.9 | 5.2 | 10.9 |
| HFC-1234ze-E | 73.8 | 72.7 | 59.0 | 70.7 | 71.5 | 61.1 |
| HFC-1234ze-Z | 12.5 | 13.5 | 12.0 | 16.4 | 19.9 | 24.0 |
| HFC-245cb |  | 0.1 | 0.3 | 0.4 | 0.1 | 0.2 |
| HFC-245fa | 1.1 | 1.4 | 17.5 | 8.2 | 2.2 | 1.9 |
| Others |  |  | 0.1 | 0.4 | 1.1 | 1.9 |

The invention claimed is:

1. A process for preparing 2,3,3,3-tetrafluoropropene represented by $CF_3CF\!=\!CH_2$ and 1,3,3,3-tetrafluoropropene represented by $CF_3CH\!=\!CHF$, the process comprising reacting 3,3,3-trifluoropropyne represented by the chemical formula $CF_3C\equiv CH$ with hydrogen fluoride under heating.

2. The process according to claim 1, wherein the reaction is carried out in a gas phase.

3. The process according to claim 1, wherein the reaction is carried out in the presence of a catalyst.

4. The process according to claim 1, wherein the reaction is carried out in the presence of chromium oxide or fluorinated chromium oxide as a catalyst.

5. The process according to claim 2, wherein the reaction is carried out in the presence of a catalyst.

6. The process according to claim 2, wherein the reaction is carried out in the presence of chromium oxide or fluorinated chromium oxide as a catalyst.

7. The process according to claim 3, wherein the reaction is carried out in the presence of chromium oxide or fluorinated chromium oxide as a catalyst.

8. The process according to claim 5, wherein the reaction is carried out in the presence of chromium oxide or fluorinated chromium oxide as a catalyst.

* * * * *